United States Patent [19]

Berntsson et al.

[11] 4,045,563
[45] Aug. 30, 1977

[54] SUBSTITUTED 2-[PYRIDYLALKYLENESULFINYL]-BENZIMIDAZOLES WITH GASTRIC ACID SECRETION INHIBITING EFFECTS

[75] Inventors: Peder Bernhard Berntsson, Molndal; Stig Åke Ingemar Carlsson; Lars Erik Garberg, both of Molnlycke; Ulf Krister Junggren, Pixbo; Sven Erik Sjöstrand, Kungsbacka; Gunhild Wika von Wittken Sundell, Askim, all of Sweden

[73] Assignee: AB Hässle, Goteborg, Sweden

[21] Appl. No.: 630,916

[22] Filed: Nov. 11, 1975

[51] Int. Cl.² ............... A61K 31/44; C07D 235/12
[52] U.S. Cl. .................. 424/263; 260/283 R; 260/283 CN; 260/287 R; 260/293.6; 260/294.8 C; 260/302 H; 260/306.7 R; 260/309.2; 548/327; 548/328; 424/258; 424/270; 424/273 R
[58] Field of Search .................. 260/294.8 C; 424/263

[56] References Cited

FOREIGN PATENT DOCUMENTS 1,804,450  3/1970  Germany ............ 260/294.8 C

*Primary Examiner*—Alan L. Rotman
*Attorney, Agent, or Firm*—Brumbaugh, Graves, Donohue & Raymond

[57] ABSTRACT

Compounds having the structural formula

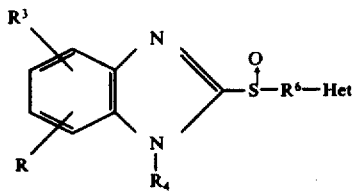

pharmaceutical compositions containing the same, and the use thereof for affecting gastric acid secretion; intermediate products having the structural formula

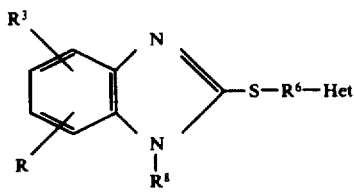

and methods for preparing the same.

65 Claims, No Drawings

SUBSTITUTED 2-[PYRIDYLALKYLENESULFINYL]-BENZIMIDAZOLES WITH GASTRIC ACID SECRETION INHIBITING EFFECTS

The present invention relates to new compounds having valuable properties in affecting gastric acid secretion in mammals, including man, as well as the process for their preparation, method of affecting gastric acid secretion and pharmaceutical preparations containing said novel compounds.

The object of the present invention is to obtain compounds which affect gastric acid secretion, and which inhibit exogenously or endogenously stimulated gastric acid secretion. These compounds can be used in the treatment of peptic ulcer disease.

It has now been found that compounds of the formula below possess such properties.

A. Compounds of the invention are those of the general formula I

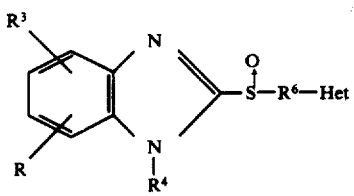

(I)

wherein R and $R^3$ are the same or different and are selected from the group consisting of hydrogen, alkyl, halogen, cyano, carboxy, carboxy-alkyl, carboalkoxy, carbo-alkoxyalkyl, carbamoyl, carbamoyloxy, hydroxy, alkoxy, hydroxy alkyl, trifluoromethyl and acyl in any position, $R^4$ is selected from the group consisting of hydrogen, alkyl, acyl, carboalkoxy, carbamoyl, alkylcarbamoyl, dialkylcarbamoyl, alkylcarbonyl methyl, alkoxycarbonyl methyl and alkylsulphonyl, $R^6$ is selected from the group consisting of a straight or branched alkylchain having 1 to 4 carbon atoms, whereby only one methylene group is present between S and Het, and Het is selected from the group consisting of imidazolyl, imidazolinyl, benzimidazolyl, thiazolyl, thiazolinyl, quinolyl, piperidyl and pyridyl, which may be further substituted preferably in the 3 to 5 position with lower alkyl groups such as methyl, ethyl and propyl and/or with halo substituents such as chloro and bromo, or its therapeutically acceptable salts.

Alkyl R and $R^3$ of formula I are suitably alkyl having up to 7 carbon atoms, preferably up to 4 carbon atoms. Thus, alkyl R may be methyl, ethyl, n-propyl, isopropyl, n-butyl, isobutyl, or t-butyl.

Halogen R and $R^3$ are fluoro, iodo, bromo or chloro, preferably bromo or chloro.

Carboxy R and $R^3$ are the group HOOC—.

Carboalkyl R and $R^3$ are the groups HOOC-alkyl wherein the alkyl group has up to 4 carbon atoms, preferably up to 2 carbon atoms. Carboxyalkyl R and $R^3$ are e.g. carboxymethyl, carboxyethyl.

Carboalkoxy R and $R^3$ are the groups alkyl-O—OC—, wherein the alkyl group has up to 4 carbon atoms, preferably up to 2 carbon atoms. Carboalkoxy R and $R^3$ are e.g. carbomethoxy ($CH_3OOC$—, carboethoxy ($C_2H_5OOC$—).

Carboalkoxy alkyl R and $R^3$ are the groups alkyl-OOC-alkyl[1], wherein the alkyl group has up to 4 carbon atoms, preferably up to 2 carbon atoms, and alkyl[1] group has up to 4 carbon atoms, preferably up to 2 carbon atoms, such as carbomethoxymethyl ($CH_3OOCCH_2$), carbomethoxyethyl ($CH_3OCC_2H_4$—), carboethoxymethyl ($C_2H_5OOCCH_2$—) and carboethoxyethyl ($C_2H_5OOCC_2H_4$—).

Carbamoyl R and $R^3$ are the group $H_2NCO$—.

Carbamoylalkyl R and $R^3$ are the groups $H_2NCO$ alkyl, wherein the alkyl group has up to 4 carbon atoms preferably up to 2 carbon atoms, such as carbamoylmethyl ($H_2NCOCH_2$—), or carbamoylethyl ($H_2NCOC_2H_4$—).

Alkoxy R and $R^3$ are suitably alkoxy groups having up to 5 carbon atoms, preferably up to 3 carbon atoms, such as methoxy, ethoxy, n-propoxy, or isopropoxy.

Hydroxyalkyl R and $R^3$ have suitably up to 7 carbon atoms, preferably up to 4 carbon atoms and are straight or branched and are e.g. hydroxy methyl, 1-hydroxypropyl-2, 1-hydroxy-ethyl-2, or 1-hydroxy-2-methylpropyl-2.

Acyl R and $R^3$ have preferably up to 4 carbon atoms and are e.g. formyl, acetyl or propionyl.

Alkyl $R^4$ is a lower straight or branched alkyl group having up to 5 carbon atoms, preferably up to 3 carbon atoms, and is e.g. methyl, ethyl, or n-propyl.

Acyl $R^4$ has preferably up to 4 carbon atoms and is e.g. formyl, acetyl or propionyl.

Carboalkoxy $R^4$ is the group alkyl —O—OC, wherein the alkyl group has up to 4 carbon atoms, preferably up to 2 carbon atoms, and is e.g. carbomethoxy ($CH_3OOC$—) or carboethoxy ($C_2H_5OOC$—).

Carbamoyl $R^4$ is the group $H_2NCO$—.

Alkylcarbamoyl $R^4$ is the group

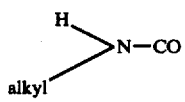

wherein the alkyl group may be straight or branched, has up to 4 carbon atoms, and is e.g. methylcarbamoyl, ethylcarbamoyl, or isopropylcarbamoyl.

Dialkylcarbamoyl $R^4$ is the group $(alkyl)_2NCO$ wherein the alkyl groups each represent an alkyl group having up to 4 carbon atoms, and is e.g. dimethylcarbamoyl, diethylcarbamoyl or N-methyl-N-ethylcarbamoyl.

Alkylcarbonylmethyl $R^4$ is the group alkyl-CO—$CH_2$—, wherein the alkyl group has up to 4 carbon atoms, and is e.g. acetylmethyl or propionylmethyl.

Alkoxycarbonylmethyl $R^4$ is the group alkyl-O—CO—$CH_2$—, wherein the alkyl group has up to 4 carbon atoms, and is e.g. methoxycarbonylmethyl, ethoxycarbonylmethyl or propoxycarbonylmethyl.

Alkylsulphonyl $R^4$ is the group alkyl-$SO_2$— wherein the alkyl group has up to 4 carbon atoms, and is e.g. methylsulphonyl, ethylsulphonyl or isopropylsulphonyl Alkyl $R^6$ is a lower straight or branched alkyl having up to 4 carbon atoms and is e.g. methyl, (methyl)methyl or (ethyl)methyl, (isopropyl)methyl or (dimethyl)methyl.

The heterocyclic group Het, may be further substituted with alkyl or halogen preferably in the 3-5 position. Such alkyl groups are preferably lower alkyl groups such as methyl, ethyl or propyl. Such halogen substituents are preferably chloro or bromo.

The heterocyclic group Het is preferably bound in the 2-position, but may also be bound in the 4-position to the rest of the molecule.

Compounds of formula I above may be prepared according to the following methods:

a. oxidizing a compound of formula II

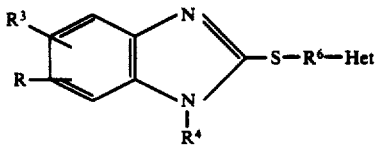
(II)

wherein R, R³, R⁴, R⁶ and Het have the meanings given, to form a compound of formula I.

b. reacting a compound of the formula III

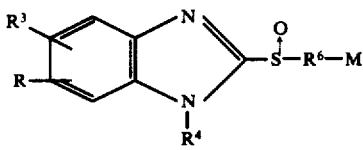
(III)

wherein R, R³, R₄ and R⁶ have the meanings given above and M is a metal selected from the group consisting of K, Na and Li, with a compound of formula IV Z—Het    (IV)

wherein Het has the same meaning as given above, Z is a reactive esterified hydroxy group, to form a compound of formula I;

c. reacting a compound of the formula V

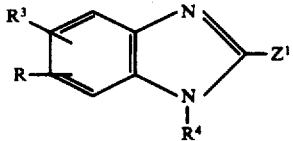
(V)

wherein R, R³ and R⁴ have the same meanings as given above and Z¹ is SH or a reactive esterified hydroxy group, with a compound of the formula VI Z²—R⁶—Het    (VI)

wherein Het and R⁶ have the same meanings as given above, and Z² is a reactive esterified hydroxy group or SH, to form an intermediate of formula II above, which then is oxidized to give a compound of formula I;

d. reacting a compound of the formula VII

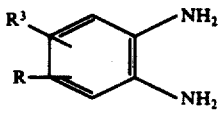
(VII)

wherein R and R³ have the same meanings as given above with a compound of the formula VIII HOOC—S—R⁶—Het    (VIII)

wherein Het and R⁶ have the same meanings as given above, to form an intermediate of formula II above, which then is oxidized to give a compound of formula I, which compound may be converted to its therapeutically acceptable salts, if so desired.

e. reacting a compound of the formula

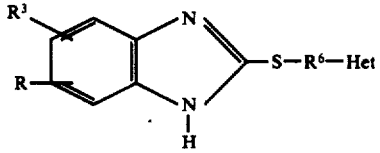

wherein R, R³, R⁶ and Het have the meanings given above, with a compound Z—R⁷, wherein R⁷ is alkyl, acyl, carboalkoxy, carbamoyl, dialkylcarbamoyl, alkylcarbonylmethyl, alkoxycarbonylmethyl, or alkylsulphonyl, to give a compound of formula II wherein R⁴ has the meaning given for R⁷, which compound is further oxidized to give a compound of formula I.

f. reacting a compound of the formula

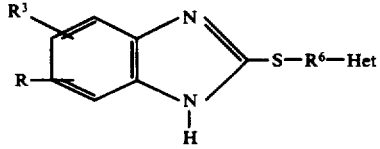

wherein R, R³, R⁶, and Het have the meanings given above with an alkylisocyanate to give a compound of formula II wherein R⁴ is alkylcarbamoyl, which compound is further oxidized to give a compound of formula I The reactions of (e) and (f) normally take place in a solvent such as acetonitrile.

In the reactions above Z, Z¹, and Z² may be a reactive, esterified hydroxy group which is a hydroxy group esterified in the presence of a strong, inorganic or organic acid, preferably a hydrohalogen acid, such as hydrochloric acid, hydrobromic acid, or hydroiodic acid, also sulfuric acid or a strong organic sulfonic acid such as a strong aromatic acid, e.g. benzenesulfonic acid, 4-bromo-benzenesulfonic acid or 4-toluenesulfonic acid.

The oxidation of the sulfur atom in the chains above to sulfinyl (S→O) takes place in the presence of an oxidizing agent selected from the group consisting of nitric acid, hydrogen peroxide, peracids, peresters, ozone, dinitrogentetroxide, iodosobenzene, N-halosuccinimide, 1-chlorobenzotriazole, t-butylhypochlorite, diazobicyclo[2,2,2] octane bromine complex, sodium metaperiodate, selenium dioxide, manganese dioxide, chromic acid, cericammonium nitrate, and sulfuryl chloride. The oxidation usually takes place in a solvent wherein the oxidizing agent is present in some excess in relation to the product to be oxidized.

Depending on the process conditions and the starting materials, the end product is obtained either as the free base or in the acid addition salt, both of which are included within the scope of the invention. Thus, basic, neutral or mixed salts may be obtained as well as hemiamino, sesqui-or polyhydrates. The acid addition salts of the new compounds may in a manner known per se be transformed into the free base using basic agents such as alkali or by ion exchange. On the other hand, the free bases obtained may form salts with organic or inorganic acids. In the preparation of acid addition salts preferably such acids are used which form suitable therapeutically acceptable salts. Such acids include hydrohalogen acids, sulfonic, phosphoric, nitric, and perchloric acids; aliphatic, alicyclic, aromatic, heterocyclic carboxy or sulfonic acids, such as formic, acetic, propionic, succinic, glycolic, lactic, malic, tartaric, citric, ascorbic, maleic, hydroxymaleic, pyruvic, phenylacetic, benzoic, p-aminobenzoic, anthranilic, p-hydroxybenzoic, salicyclic or p-aminosalicyclic acid, embonic, methanesulfonic, ethanesulfonic, hydroxyethanesulfonic, ethylene-sulfonic, halogenbenzenesulfonic, toluenesulfonic, naphthylsulfonic or sulfanilic acids; methionine, tryptophane, lysine or arginine.

These or other salts of the new compounds, such as e.g. picrates, may serve as purifying agents of the free bases obtained. Salts of the bases may be formed, separated from solution, and then the free base can be recovered from a new salt solution in a purer state. Because of the relationship between the new compounds in free base form and their salts, it will be understood that the corresponding salts are included within the scope of the invention.

Some of the new compounds may, depending on the choice of starting materials and process, be present as optical isomers or racemate, or if they contain at least two asymmetric carbon atoms, be present as an isomer mixture (racemate mixture).

The isomer mixtures (racemate mixtures) obtained may be separated into two stereoisomeric (diastereomeric) pure racemates by means of chromatography or fractional crystallization.

The racemates obtained can be separated according to known methods, e.g. recrystallization from an optically active solvent, use of micro organisms, reactions with optically active acids forming salts which can be separated, separation based on different solubilities of the diastereomers. Suitable optically active acids are the L-and D-forms of tartaric acid, di-o-tolyl-tartaric acid, malic acid, mandelic acid, camphorsulfonic acid or quinic acid. Preferably the more active part of the two antipodes is isolated.

The starting materials are known or may, if they should be new, be obtained according to processes known per se.

In clinical use the compounds of the invention are administered orally, rectally or by injection in the form of a pharmaceutical preparation which contains an active component either as a free base or as a pharmaceutically acceptable, non-toxic acid addition salt, such as hydrochloride, lactate, acetate, sulfamate, in combination with a pharmaceutically acceptable carrier. The carrier may be in the form of a solid, semisolid or liquid diluent, or a capsule. These pharmaceutical preparations are a further object of the invention. Usually the amount of active compound is between 0.1 to 95% by weight of the preparation, between 0.5 to 20% by weight in preparations for injection and between 2 and 50% by weight in preparations for oral administration.

In the preparation of pharmaceutical preparations containing a compound of the present invention in the form of dosage units for oral administration the compound selected may be mixed with a solid, pulverulent carrier, such as lactose, saccharose, sorbitol, mannitol, starch, amylopectin, cellulose derivatives or gelatin, as well as with an antifriction agent such as magnesium stearate, calcium stearate, and polyethyleneglycol waxes. The mixture is then pressed into tablets. If coated tablets are desired, the above prepared core may be coated with a concentrated solution of sugar, which may contain gum arabic, gelatin, talc, titanium dioxide or with a lacquer dissolved in volatile organic solvent or mixture of solvents. To this coating various dyes may be added in order to distinguish among tablets with different active compounds or with different amounts of the active compound present.

Soft gelatin capsules may be prepared which capsules contain a mixture of the active compound or compounds of the invention and vegetable oil. Hard gelatin capsules may contain granules of the active compound in combination with a solid, pulverulent carrier as lactose, saccharose, sorbitol, mannitol, potato starch, corn starch, amylopectin, cellulose derivatives or gelatin.

Dosage units for rectal administration may be prepared in the form of suppositories which contain the active substance in a mixture with a neutral fat base, or they may be prepared in the form of gelatin-rectal capsules which contain the active substance in a mixture with a vegetable oil or paraffin oil.

Liquid preparations for oral administration may be prepared in the form of syrups or suspensions, e.g. solutions containing from 0.2 to 20% by weight of the active ingredient and the remainder consisting of sugar and a mixture of ethanol, water, glycerol and propylene glycol. If desired, such liquid preparations may contain coloring agents, flavoring agents, saccharin and carboxymethylcellulose as a thickening agent.

Solutions for parenteral administration by injection may be prepared as an aqueous solution of a water soluble pharmaceutically acceptable salt of the active compound, preferably in a concentration from 0.5 to 10% by weight. These solutions may also contain stabilizing agents and/or buffering agents and may be manufactured in different dosage unit ampoules.

Pharmaceutical tablets for oral use are prepared in the following manner: The solid substances are ground or seived to a certain particle size, and the binding agent is homogenized and suspended in a suitable solvent. The therapeutically compounds and auxiliary agents are mixed with the binding agent solution. The resulting mixture is moistened to form a uniform suspension having the consistency of wet snow. The moistening causes the particles to aggregate slightly, and the resulting mass is pressed through a stainless steel sieve having a mesh size of approximately 1 mm. The layers of the mixture are dried in carefully controlled drying cabinets for approximately ten hours to obtain the desired particle size and consistency. The granules of the dried mixture are sieved to remove any powder. To this mixture, disintegrating, antifriction and antiadhesive agents are added. Finally, the mixture is pressued into tablets using a machine with the appropriate punches and dies to obtain the desired tablet size. The pressure applied affects the size of the tablet, its strength and its ability to dissolve in water. The compression pressure used should be in the range 0.5 to 5 tons. Tablets are manufactured at the rate of 20,000 to 200,000 per hour. The tablets, especially those which are rough or bitter may be coated with a layer of sugar or some other palatable substance. They are then packaged by machines having electronic counting devices. The different types of packages consist of glass or plastic gallipots, boxes, tubes and specific dosage adapted packages.

The typical daily dose of the active substance varies according to the individuals needs and the manner of administration. In general, oral dosages range from 100 to 400 mg/day of active substance and intravenous dosages range from 5 to 20 mg/day.

The following illustrates a preferred embodiment of the invention without being limited thereto. Temperature is given in degrees Centigrade.

The starting materials in the examples found below were prepared in accordance with the following methods: (1) a 1,2-diamino compound, such as o-phenylenediamine was reacted with potassium ethylxanthate (according to Org. Synth. Vol. 30 p. 56) to form a 2-mercaptobenzimidazole; 2) the compound 2-chloromethylpyridine was prepared by reacting 2-hydroxymethylpyridine with thionylchloride (according to Arch. Pharm. Vol. 26, pp. 448–451 (1956); (3) the compound 2-chloromethylbenzimidzole was prepared by condensing o-phenylenediamine with chloroacetic acid.

EXAMPLE 1

28.9 g of 2-[2-pyridylmethylthio]-benzimidazole were dissolved in 160 ml of $CHCl_3$, 24.4 g of m-chloroperbenzoic acid were added in portions while stirring and cooling to 5° C. After 10 minutes, the precipitated m-chlorobenzoic acid was filtered. The filtrate was diluted with $CH_2Cl_2$, washed with a $Na_2CO_3$ solution, dried over $Na_2SO_4$ and evaporated in vacuo. The resiude crystallize when diluted with $CH_3CN$, and 2-[2-pyridylmethylsulfinyl]-benzimidazole was recrystallized from $CH_3CN$. Yield 22.3 g; m.p. 150°–154° C.

EXAMPLES 2–30

The preparation of compounds of formula I labelled 2–30 was carried out in accordance with Example 1 above. The compounds prepared are listed in Table 1 which identifies the substituents for these compounds.

EXAMPLE 31

(method c)

0.1 Moles of 4-methyl-2-mercaptobenzimidazole were dissolved in 20 ml of water and 200 ml of ethanol containing 0.2 moles of sodium hydroxide. 0.1 moles of 2-chloro-methylpyridine hydrochloride were added and the mixture was refluxed for 2 hours. The sodium chloride formed was filtered off and the solution was evaporated in vacuo. The residue was dissolved in acetone and was treated with active carbon. An equivalent amount of concentrated hydrochloric acid was added, whereupon the mono-hydrochloride of 2-[2-pyridylmethylthio]-(4-methyl)-benzimidazole was isolated. Yield 0.05 moles; melting point 137° C.

This compound was then oxidized in accordance with Example 1 above.

EXAMPLE 32

(method b)

0.1 Moles of Li-methylsulfinylbenzimidazole were dissolved in 150 mls of benzene. 0.1 moles of 2-chloropyridine was added and the mixture was refluxed for 2 hours. The lithiumchloride formed was filtered off, and the solution was evaporated in vacuo. The residue was crystallized from $CH_3CN$, and recrystallized from the same solvent. Yield: 0.082 moles of 2-[2-pyridylmethylsulfinyl]-benzimidazole melting at 151°–154° C.

EXAMPLE 33

(method d)

18.3 g of 2-[(2-pyridine)methylthio] formic acid and 10.8 g of o-phenylenediamine were boiled for 40 minutes in 100 ml of 4N HCl. The mixture was cooled and neutralized with ammonia. The neutral solution was then extracted with ethyl acetate. The organic phase was treated with active carbon and evaporated in vacuo. The residue was dissolved in acetone, whereupon an equivalent of concentrated HCl was added. The precipitated hydrochloride was filtered off after cooling and the salt was recrystallized from absolute ethanol and some ether. Yield of 2-[2-(pyridyl)methylthio]-benzimidazole was 4.3 g.

This compound was then oxidized in accordance with Example 1 above.

EXAMPLE 34

(method e)

13.5 g (0.05 moles) of 2-[pyridylmethylthio]-benzimidazole hydrochloride, 3.9 g (0.05 moles) of acetylchloride, and 10.1 g (0.1 moles) of triethylamine were dissolved in 100 ml of acetonitrile. The mixture was heated in a 40° C. waterbath for 30 minutes. After cooling, the crystals formed were filtered off and were suspended in water in order to dissolve the triethylamine hydrochloride. The resiude, 2-[2-pyridylmethylthio]-N-acetylbenzimidazole was filtered off. Yield 7.2 g (51%); m.p. 119–24° C. as base.

This compound was then oxidized in accordance with Example 1 above.

EXAMPLE 35

2-[2-pyridylmethylthio]-N-methoxycarbonylbenzimidazole was prepared in accordance with Example 34 above. Mp. 78° C.

This compound was then oxidized in accordance with Example 1 above. Mp. 135° C.

EXAMPLE 36

(method c)

16.2 g of 2-mercaptobenzimidazole and 16.4 g of chloromethylpyridine hydrochloride were dissolved in 200 ml of 95% ethenol, 8 g of sodium hydroxide in 20 ml of water were added, whereupon the solution was refluxed for 2 hours. The sodium chloride formed was filtered off and the solution was evaporated in vacuo. The residue, 2-[2-pyridylmethylthio]benzimidazole, was recrystallized from 70% ethanol. Yield: 9 g.

This compound was then oxidized in accordance with Example 1 above.

EXAMPLE 37

2-[2-pyridylmethylsulfinyl]-(N-carbamoyl)-benzimidazole was prepared from 2-[2-pyridylmethylthio]-benzimidazole and carbamoylchloride, whereupon the thio-compound obtained was oxidized in accordance with Example 1, to the corresponding sulfinyl compound. Mp. 164° C.

EXAMPLE 38

(method f)

4.82 g (0.02 moles) of 2-[2-pyridylmethylthio]-benzimidazole and 1.5 g of methylisocyanate were refluxed in 150 mls of toluene for 2 hrs. The mixture was cooled, the precipitate formed filtered off and recrystallized from toluene. Yield of 2-[2-pyridylmethylthio]-(N-methylcarbamoyl)-benzimidazole as 4.5 g. Mp: 135° C. The thio-compound was oxidized to the corresponding sulphinyl-compound in accordance with Example 1 above. Mp. of 2-[2-pyridylmethylsulphinyl]-(N-methylcarbamoyl)-benzimidazole was 140° C.

EXAMPLE 39

12.0 g (0.05 moles) of 2-[2-pyridylmethylthio]-benzimidazole, 8.0 g (0.058 moles) of $K_2CO_3$ and 5.5 g (0.059 moles) of 1-chloro-2-propanone were refluxed in 200 mls of acetonitrile for 2 hrs. The solution was then filtered and evaporated. The residue, 2-[2-pyridylmethylthio]-(N-acetylmethyl)-benzimidazole was recrystallized from carbon tetrachloride. Yield: 8 g. Mp.: 113° C.

The thio-compound was oxidized to the corresponding sulphinyl compound in accordance with Example 1 above.

EXAMPLE 40

2-[2-pyridylmethylthio]-(N-ethoxycarbonylmethyl)-benzimidazole was prepared in accordance with Example 34 above from 2-[2-pyridylmethylthio]-benzimidazole and chloroacetic acid ethyl ester.

The thio-compound was then oxidized to the corresponding sulphinyl compound.

EXAMPLE 41

4.82 g (0.02 moles) of 2-[2-pyridylmethylthio]-benzimidazole and 4.05 g (0.04 moles) of triethylamine were dissolved in 200 mls of acetonitrile. 2.52 g (0.022 moles) of methylsulphonic chloride in 20 mls of acetonitrile were added dropwise, whereupon the solution was left to stand overnight. The mixture was poured onto ice, whereupon the product crystallized. Recrystallization of 2-[2-pyridylmethylthio]-(N-methylsulphonyl)-benzimidazole was made from acetonitrile. Yield: 3.7 g. Mp.: 142° C.

The thio-compound was oxidized to give the corresponding sulphinyl-compound. Mp. of 2-[2-pyridylmethylsulphinyl]-(N-methylsulphonyl)-benzimidazole is 144° C.

TABLE I

Compounds of Formula I prepared

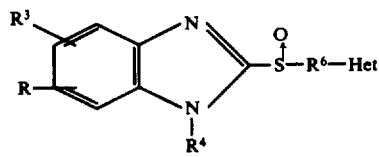

| Ex. | $R^3$ | R | $R^4$ | $R^6$ | Het | M.P.° C. |
|---|---|---|---|---|---|---|
| 1 | H | H | H | $CH_2$ | 2-pyridyl | 150–154 |
| 2 | 6-$CH_3$ | 4-$CH_3$ | H | $CH_2$ | 2-pyridyl | 141 |
| 3 | H | 5-$C_2H_5$ | H | $CH_2$ | 2-pyridyl | 90 |
| 4 | 6-Cl | 4-$CH_3$ | H | $CH_2$ | 2-pyridyl | 165 |
| 5 | H | 5-$OCH_3$ | H | $CH_2$ | 2-pyridyl | 113 |
| 6 | H | 5-OH | H | $CH_2$ | 2-pyridyl | |
| 7 | H | 5-$COCH_3$ | H | $CH_2$ | 2-pyridyl | 172 |
| 8 | H | 5-COOH | H | $CH_2$ | 2-pyridyl | |
| 9 | H | 5-$COOC_2H_5$ | H | $CH_2$ | 2-pyridyl | 171 |
| 10 | H | H | H | $CH_2$ | 2-(4-chloro)pyridyl | 163 |
| 11 | H | H | H | $CH_2$ | 2-(5-methyl)pyridyl | |
| 12 | H | H | H | $CH_2$ | 2-piperidyl | |
| 13 | H | H | H | $CH_2$ | 2-quinolyl | |
| 14 | H | H | $CH_3$ | $CH_2$ | 2-pyridyl | 113 |
| 15 | H | H | H | $CH_2$ | 4-(5-methyl)imidazolyl | |
| 16 | H | H | H | $CH(CH_3)$ | 2-pyridyl | 135 |
| 17 | H | 4-$CH_3$ | H | $CH_2$ | 2-pyridyl | |
| 18 | H | H | $COCH_3$ | $CH_2$ | 2-yridyl | |
| 19 | H | H | $COOCH_3$ | $CH_2$ | 2-pyridyl | 135 |
| 20 | H | H | H | $CH_2$ | 2-benzimidazolyl | |

| Ex. | $R^3$ | R | $R^4$ | $R^6$ | Het | M.P.° C. |
|---|---|---|---|---|---|---|
| 21 | H | 5-$CH_3$ | H | $CH_2$ | 2-pyridyl | 114 |
| 21a | H | H | H | $CH_2$ | 2-(4-methyl)pyridyl | 50 |
| 21b | H | 5-$C(CH_3)_3$ | H | $CH_2$ | 2-(5-methyl)pyridyl | 186 |
| 21c | H | 5-Br | H | $CH_2$ | 2-pyridyl | 157 |
| 21d | H | 5-$CH(CH_3)_2$ | H | $CH_2$ | 2-(5-methyl)pyridyl | ~165 |
| 21e | H | 5-Cl | H | $CH_2$ | 2-(5-methyl)pyridyl | 162 |
| 21f | H | 5-$CF_3$ | H | $CH_2$ | 2-pyridyl | 161 |
| 22 | H | 5-Cl | H | $CH_2$ | 2-pyridyl | 142 |
| 23 | H | 5-$CH(CH_3)_2$ | H | $CH_2$ | 2-pyridyl | 135 |
| 24 | H | 5-$C(CH_3)_3$ | H | $CH_2$ | 2-pyridyl | 180 |
| 25 | H | 5-$C_3H_7$ | H | $CH_2$ | 2-pyridyl | 110 |
| 26 | H | 5-$CH_3$ | H | $CH_2$ | 2-(5-methyl)pyridyl | 145 |
| 27 | H | 6-Cl | H | $CH_2$ | 2-pyridyl | 163 |
| 28 | H | H | H | $CH(C_2H_5)$ | 2-pyridyl | 134–142 |
| 29 | H | 5-Cl | H | $CH(C_2H_5)$ | 2-pyridyl | 51–59 |
| 30 | H | 5-$C_2H_5$ | H | $CH(CH_3)$ | 2-pyridyl | 144 |
| 37 | H | H | —$CONH_2$ | $CH_2$ | 2-pyridyl | 164 |
| 38 | H | H | —$CONH(CH_3)$ | $CH_2$ | 2-pyridyl | 140 |
| 39 | H | H | —$CH_2COCH_3$ | $CH_2$ | 2-pyridyl | |
| 40 | H | H | —$CH_2COOC_2H_5$ | $CH_2$ | 2-pyridyl | |
| 41 | H | H | —$SO_2CH_3$ | $CH_2$ | 2-pyridyl | 144 |
| 42 | H | 5-$CH_3$ | H | $CH_2$ | 2-(4-methyl)pyridyl | |
| 43 | H | H | H | $CH_2$ | 2-(3-methyl)pyridyl | 190 |
| 44 | H | 5-$CH_3$ | H | $CH_2$ | 2-(5-ethyl)pyridyl | 138 |

TABLE I-continued
Compounds of Formula I prepared

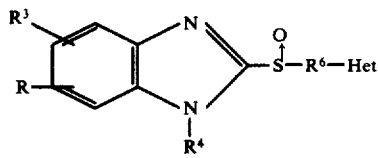

| | R | R³ | R⁴ | R⁶ | Het | |
|---|---|---|---|---|---|---|
| 45 | H | H | H | CH₂ | 2-(5-ethyl)pyridyl | 152 |
| 46 | H | 5-C₂H₅ | H | CH(C₂H₅) | 2-pyridyl | |
| 47 | H | 5-CH₃ | H | CH(CH₃) | 2-pyridyl | |
| 48 | H | 5-CN | H | CH(CH₃) | 2-pyridyl | |
| 49 | H | 5-CF₃ | H | CH(CH₃) | 2-pyridyl | |
| 50 | H | 5-CH₃ | H | CH(C₂H₅) | 2-pyridyl | |
| 51 | H | 5-CN | H | CH(C₂H₅) | 2-pyridyl | |
| 52 | H | 5-CF₃ | H | CH(C₂H₅) | 2-pyridyl | |
| 53 | H | 4-Cl | H | CH₂ | 2-pyridyl | 163 |
| 54 | H | H | H | CH[CH(CH₃)₂] | 2-pyridyl | 80 |
| 55 | 6-CH₃ | 5-CH₃ | H | CH(CH₃) | 2-pyridyl | |
| 56 | 6-CH₃ | 5-CH₃ | H | CH₂ | 2-pyridyl | 163 |

BIOLOGICAL EFFECT

The compounds of the invention possess worthwhile therepeutic properties as gastric acid secretion agents as demonstrated by the following tests. To test the gastric acid secretion activity, a modified perfusion technique was performed using dogs as test animals. An anesthetized dog was fitted with one tube going through the esophagus to the stomach for instillation of fluid, and a second tube extending through the duodenum by way of the ligated pylorus for fluid drainage. Every 15 minutes, 5 ml/kg body weight of a saline solution was introduced into the test animal, and drained samples collected and titrated to pH 7.0 with 0.04N NaOH using a radiometer automatic titrator to calculate the acid output.

Gastric acid secretion was induced by pentagastrin by administering 1-2 μg/kg per hour, giving a submaximal secretory response. Test compounds in a 0.5% Methocel (methyl cellulose) suspension were introduced into the duodenum close to the ligation at least two hours following onset of stimulation, when the secretion had reached a steady level for three consecutive 15 minute periods. The gastric secretion response was noted, and it was found that 2-[2-pyridylmethylsulfinyl]-benzimidazole inhibited gastric acid secretion to 90% when administered in an amount of 1 mg per kg body weight.

The following gastric acid inhibiting effect data were obtained for a number of compounds tested according to the method described.

Table I

| Compound | | Dose mg/kg | % inhibition |
|---|---|---|---|
| Ex. | 26 | 5 | >75 |
| | 21 | 5 | 95 |
| | 21 | 1 | 50 |
| | 2 | 5 | 94 |
| | 3 | 5 | 50 |
| | 23 | 10 | 80 |
| | 25 | 5 | 15 |
| | 22 | 5 | 35 |
| | 9 | 5 | 8 |
| | 4 | 10 | 41 |
| | 16 | 5 | 96 |
| | 16 | 1 | 37 |
| | 28 | 5 | 80 |
| | 28 | 2 | 65 |
| | 30 | 5 | 60 |
| | 42 | 5 | >75 |
| | 43 | 5 | >75 |
| | 44 | 5 | 95 |
| | 45 | 5 | 90 |
| | 53 | 5 | 30 |
| | 55 | 5 | 30 |

EXAMPLE 57

A syrup containing 2% (weight per volume of active substance was prepared from the following ingredients:

| | |
|---|---|
| 2-[2-pyridylmethylsulfinyl]-4-methylbenzimidazole | 2.0 g |
| Saccharin | 0.6 g |
| Sugar | 30.0 g |
| Glycerin | 5.0 g |
| Flavoring agent | 0.1 g |
| Ethanol 96% | 10.0 ml |
| Distilled Water (sufficient to obtain a final volume of 100 ml) | |

Sugar, Saccharin and the acid addition salt were dissolved in 60 g of warm water. After cooling, glycerin and a solution of flavoring agents dissolved in ethanol were added. To the mixture water was added to obtain a final volume of 100 ml.

The above given active substance may be replaced with other pharmaceutically acceptable acid addition salts.

EXAMPLE 58

2-[2-pyridylmethylsulfinyl]-benzimidazole . HCl (250 g) was mixed with lactose (175.8 g), potato starch (169.7 g) and colloidal silicic acid (32 g). The mixture was moistened with 10% solution of gelatin and was ground through a 12-mesh sieve. After drying, potato starch (160 g), talc (50 g) and magnesium stearate (5 g) were added and the mixture thus obtained was pressed into tablets (10,000), with each tablet containing 25 mg of active substance. Tablets can be prepared that contain any desired amount of the active ingredient.

EXAMPLE 59

Granules were prepared from 2-[2-benzimidazolyl-methylsulfinyl]-imidazolinyl-p-hydroxybenoate (250 g), lactose (175.9 g) and an alcoholic solution of polyvinyl-pyrrolidone (25 g). After drying, the granules were mixed with talc (25 g), potato starch (40 g), and magnesium stearate (2.50 g) and were pressed into 10,000 tablets. These tablets are first coated with a 10% alcoholic solution of shellac and thereupon with an aqueous solution containing saccharose (45%), gum arabic (5%), gelatin (4%), and dyestuff (0.2%). Talc and powdered sugar were used for powdering after the first five coatings. The coating was then covered with a 66% sugar syrup and polished with a solution of 10% carnauba wax in carbon tetrachloride.

EXAMPLE 60

2-[4-(5-methyl)-imidazolyylmethylsulfinyl]-benzimidazole-hydroxhloride (1 g), sodium chloride (0.8 g) and ascorbic acid (0.1 g) were dissolved in sufficient amount of distilled water to give 100 ml of solution. This solution, which contains 10 mg of active substance for each ml, was used in filling ampoules, which were sterilized by heatin at 120° C. for 20 minutes.

We claim:

1. A compound of formula I

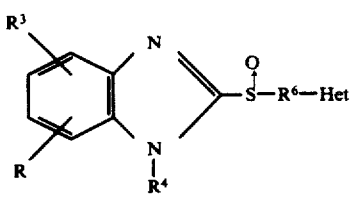

(I)

or a therapeutically acceptable salt thereof in which R is selected from the group consisting of hydrogen, alkyl having up to four carbon atoms, halogen of the group consisting of fluoro, iodo, bromo and chloro, cyano, carboxy, carboxyalkyl in which the alkyl group has up to 4 carbon atoms, carboalkoxy in which the alkyl group has up to 4 carbon atoms, carboalkoxyalkyl wherein each of the alkyl groups has up to 4 carbon atoms, carbamoyl, carbamoylalkyl in which the alkyl group has up to 4 carbon atoms, hydroxy, alkoxy having up to 5 carbon atoms, hydroxyalkyl having up to 7 carbon atoms, trifluoromethyl and alkanoyl having up to 4 carbon atoms in any position; $R^3$ is selected from the group consisting of hydrogen, alkyl having up to four carbon atoms, halogen of the group consisting of fluoro, iodo, bromo and chloro, carboxy, carboxyalkyl in which the alkyl group has up to 4 carbon atoms, carboalkoxy in which the alkyl group has up to 4 carbon atoms, carboalkoxyalkyl wherein each of the alkyl groups has up to 4 carbon atoms, carbamoyl, carbamoylalkyl in which the alkyl group has up to 4 carbon atoms, hydroxy, alkoxy having up to 5 carbon atoms, hydroxyalkyl having up to 7 carbon atoms, trifluoromethyl and alkanoyl having up to 4 carbon atoms in any position; $R^4$ is selected from the group consisting of hydrogen, alkyl straight or branched chain having up to 5 carbon atoms, alkanoyl having up to 4 carbon atoms, carbamoyl, alkylcarbamoyl wherein the alkyl group may be straight or branched and has up to 4 carbon atoms, dialkylcarbamoyl wherein each alkyl group has up to 4 carbon atoms, alkylcarbonylmethyl wherein the alkyl group has up to 4 carbon atoms, alkoxycarbonylmethyl wherein the alkyl group has up to 4 carbon atoms, and alkylsulphonyl wherein the alkyl group has up to 4 carbon atoms; $R^6$ is a straight or branched alkyl group having 1 to 4 carbon atoms, wherein at most one methylene group is present between S and Het, and Het is pyridyl, which may be further substituted preferably in the 3 to 5 position with lower alkyl groups such as methyl, ethyl or propyl or with halogen substituents such as chloro and bromo.

2. A compound according to claim 1 or a therapeutically acceptable salt thereof in which R is hydrogen, hydroxy, cyano, methyl, ethyl, n-propyl, isopropyl, t-butyl, trifluoromethyl, methoxy, acetyl, carboxy, carbethoxy, $R^3$ is hydrogen, methyl or chloro, $R^4$ is hydrogen, methyl, carbamoyl, methylcarbamoyl, methylcarbonylmethyl, ethoxycarbonylmethyl or methylsulfonyl, $R^6$ is $CH_2$ and Het is 2-pyridyl, which may be further substituted with methyl, ethyl or chloro.

3. A compound according to claim 1 or a therapeutically acceptable salt thereof in which R is hydrogen, methyl, ethyl trifluoromethyl, cyano or chloro; $R^3$ is hydrogen, methyl, ethyl, trifluoromethyl or chloro; $R^4$ is hydrogen, $R^6$ is $CH(CH_3)$; and Het is 2-pyridyl, which may be further substituted with methyl, ethyl or chloro.

4. A compound according to claim 1 or a therapeutically acceptable salt thereof in which R is hydrogen, methyl, ethyl, trifluoromethyl, cyano or chloro; $R^3$ is hydrogen, methyl, ethyl, trifluoromethyl or chloro; $R^4$ is hydrogen, $R^6$ is $CH(C_2H_5)$; and Het is 2-pyridyl, which may be further substituted with methyl, ethyl or chloro.

5. A compound according to claim 1 or a therapeutically acceptable salt thereof in which R is hydrogen, methyl, ethyl, trifluoromethyl, cyano or chloro; $R^3$ is hydrogen, methyl, ethyl, trifluoromethyl or chloro; $R^4$ is hydrogen; $R^6$ is CH; and Het is 2-pyridyl, which may be further substituted with methyl, ethyl or chloro.

6. A compound selected from the group consisting of:
2-[2-pyridylmethylsulfinyl]benzimidazole,
2-[2-pyridylmethylsulfinyl]-(4,6dimethyl)benzimidazole
2-[2-pyridylmethylsulfinyl]-(5-ethyl)benzimidazole,
2-pyridylmethylsulfinyl]-(4-methyl, 6-chloro)benzimidazole,
2-[2-pyridylmethylsulfinyl]-(5-methoxy)benzimidazole,
2-[2-pyridylmethylsulfinyl]-(5-hydroxy)benzimidazole,
2-[2-pyridylmethylsulfinyl]-(5-acetyl)benzimidazole,
2-[2-pyridylmethylsulfinyl]-(5-carboxy)benzimidazole,
2-[2-pyridylmethylsulfinyl]-(5-carbethoxy)benzimidazole,
2-[2-(4-chloro)pyridyl-methylsulfinyl]benzimidazole),
2-[2-(5-methyl)pyridylmethylsulfinyl]benzimidazole,
2-[2-pyridylmethylsulfinyl]-N-methylbenzimidazole),
2-[2pyridyl-(methyl)methylsulfinyl]benzimidazole,
2-[2-pyridylmethylsulfinyl]-(4-methyl)benzimidazole,
2-[2-pyridylmethylsulfinyl]-(N-acetyl)benzimidazole,
2-[2-pyridylmethylsulfinyl]-(N-methoxycarbonyl)-benzimidazole,
2-[2-pyridylmethylsulfinyl]-(5methyl)benzimidazole,
2-[2-pyridylmethylsulfinyl]-(5-chloro)benzimidazole,
2-[2-pyridylmethylsulfinyl]-(5-isopropyl)benzimidazole,
2-[2-pyridylmethylsulfinyl]-(5-t-butyl)benzimidazole,
2-[2-pyridylmethylsulfinyl]-(5-n-propyl)benzimidazole,
2-[2-pyridylmethylsulfinyl]-(N-carbamoyl)benzimidazole,
2-[2-pyridylmethylsulfinyl]-(N-methylcarbamoyl)-benzimidazole,
2-[2-pyridylmethylsulfinyl]-(N-acetylmethyl)benzimidazole,
2-[2-pyridylmethylsulfinyl]-(N-ethoxycarbonylmethyl)benzimidazole,
2-[2-pyridylmethylsulfinyl]-(N-methylsulfonyl)benzimidazole, 2-[2(4-methyl)pyridylmethylsulfinyl]-(5-methyl)benzimidazole,
2-[2-(5-methyl)pyridylmethylsulfinyl]-(5-methyl)benzimidazole,
2-[2-pyridylmethylsulfinyl]-(6-chloro)benzimidazole,
2-[2-pyridyl-(ethyl)methylsulfinyl]benzimidazole,
2-[2-pyridyl-(ethyl)methylsulfinyl]-(5-chloro)benzimidazole,
2-[2-pyridyl-(methyl)methylsulfinyl]-5-ethyl)benzimidazole,
2-[2-(3-methyl)pyridylmethylsulfinyl]benzimidazole,
2-[2-(5-ethyl)pyridylmethylsulfinyl]-(5-methyl)benzimidazole,
2-[2-(5-ethyl)pyridylmethylsulfinyl]benzimidazole,
2-[2pyridyl-(ethyl)methylsulfinyl]-(5-ethyl)benzimidazole,
2-[2-pyridyl-(methyl)methylsulfinyl]-(5-methyl)benzimidazole,
2-[2-pyridyl-(methyl)methylsulfinyl]-(5-cyano)benzimidazole,
2[2pyridyl-(methyl)methylsulfinyl]-(5-trifluoro)benzimidazole,
2-[2-pyridyl-(ethyl)methylsulfinyl]-5-methyl)benzimidazole,
2-[2-pyridyl-(ethyl)methylsulfinyl]-(5-cyano)benzimidazole,
2-[2-pyridyl-(ethyl)methylsulfinyl]-(5-trifluoro)benzimidazole,
2-[2-pyridylmethylsulfinyl]-(4-chloro)benzimidazole,
2-[2-pyridyl-(isopropyl)methylsulfinyl]benzimidazole,
2-[2-pyridyl-(methyl)methylsulfinyl]-(5,6-dimethyl)benzimidazole, and
2-[2-pyridylmethylsulfinyl]-(5,6-dimethyl)benzimidazole,
and a therapeutically acceptable salt thereof.

7. A method of inhibiting gastric acid secretion by administering to mammals, including man, suffering from gastric acid secretion disturbances a compound of the formula I

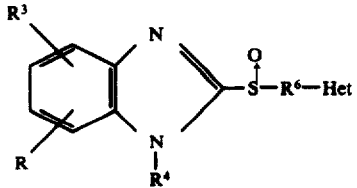

(I)

or a therapeutically acceptable salt thereof in which R is selected from the group consisting of hydrogen, alkyl having up to four carbon atoms, halogen of the group consisting of fluoro, iodo, bromo and chloro, cyano, carboxy, carboxyalkyl in which the alkyl group has up to 4 carbon atoms, carboalkoxy in which the alkyl group has up to 4 carbon atoms, carboalkoxyalkyl wherein each of the alkyl groups has up to 4 carbon atoms, carbamoyl, carbamoylalkyl in which the alkyl group has up to 4 carbon atoms, hydroxy, alkoxy having up to 5 carbon atoms, hydroxyalkyl having up to 7 carbon atoms, trifluoromethyl and alkanoyl having up to 4 carbon atoms in any position; $R^3$ is selected from the group consisting of hydrogen, alkyl having up to four carbon atoms, halogen of the group consisting of fluoro, iodo, bromo and chloro, carboxy, carboxyalkyl in which the alkyl group has up to 4 carbon atoms, carboalkoxy in which the alkyl group has up to 4 carbon atoms, carboalkoxyalkyl wherein each of the alkyl groups has up to 4 carbon atoms, carbamoyl, carbamoylalkyl in which the alkyl group has up to 4 carbon atoms, hydroxy, alkoxy having up to 5 carbon atoms, hydroxyalkyl having up to 7 carbon atoms, trifluoromethyl and alkanoyl having up to 4 carbon atoms in any position; $R^4$ is selected from the group consisting of hydrogen, alkyl straight or branched chain having up to 5 carbon atoms, alkanoyl having up to 4 carbon atoms, carboalkoxy wherein the alkyl group has up to 4 carbon atoms, carbamoyl, alkylcarbamoyl wherein the alkyl group may be straight or branched and has up to 4 carbon atoms, dialkylcarbamoyl wherein each alkyl group has up to 4 carbon atoms, alkyl carbonylmethyl wherein the alkyl group has up to 4 carbon atoms, alkoxycarbonylmethyl wherein the alkyl group has up to 4 carbon atoms, and alkylsulphonyl wherein the alkyl group has up to 4 carbon atoms; $R^6$ is a straight or branched alkyl group having 1 to 4 carbon atoms, wherein at most one methylene group is present between S and Het, and Het is pyridyl, which may be further substituted preferably in the 3 to 5 position which lower alkyl groups such as methyl, ethyl and propyl or with halo substituents such as chloro and bromo, in amount sufficient to inhibit such suffering.

8. A method according to claim 7, wherein in said compound of formula I, R is hydrogen, hydroxy, cyano, methyl, ethyl, n-propyl, isopropyl, methoxy, tert-butyl, trifluoromethyl, acetyl, carboxy or carboethoxy, $R^3$ is hydrogen, methyl or chloro, $R^4$ is hydrogen, methyl, acetyl, carbomethoxy, carbamoyl, methylcarbamoyl, methylcarbonylmethyl, ethoxycarbonylmethyl or methylsulphonyl, $R^6$ is $CH_2$ and Het is 2-pyridyl, which may be further substituted with methyl, ethyl or chloro.

9. A method according to claim 7, wherein in said compound of formula I, R is hydrogen, methyl, ethyl, trifluoromethyl, cyano or chloro; $R^3$ is hydrogen, methyl, ethyl, trifluoromethyl or chloro; $R^4$ is hydrogen; $R^6$ is $CH(CH_3)$; and Het is 2-pyridyl which may be further substituted with methyl, ethyl or chloro.

10. A method according to claim 7, wherein in said compound of formula I, R is hydrogen, methyl, ethyl, cyano, trifluoromethyl or chloro; $R^3$ is hydrogen, methyl, ethyl, trifluoromethyl or chloro; $R^4$ is hydrogen, $R^6$ is $CH(C_2H_5)$ and Het is 2-pyridyl, which may be further substituted with methyl, ethyl, or chloro.

11. A method according to claim 7, wherein in said compound of formula I, R is hydrogen, methyl, ethyl, trifluoromethyl, cyano or chloro; $R^3$ is hydrogen, methyl, ethyl, trifluoromethyl or chloro; $R^4$ is hydrogen; $R^6$ is $CH[CH(CH_3)_2]$ and Het is 2-pyridyl which may be further substituted with methyl, ethyl or chloro.

12. A method according to claim 7, wherein said compound of formula I is selected from the group consisting of
2-[2-pyridylmethylsulfinyl]-benzimidazole,
2-[2-pyridylmethylsulfinyl]-(4,6-dimethyl)benzimidazole,
2-[2-pyridylmethylsulfinyl]-(5-ethyl)benzimidazole,
2-[2-pyridylmethylsulfinyl]-(4-methyl, 6-chloro)benzimidazole,
2-[2-pyridylmethylsulfinyl]-(5-methoxy)benzimidazole,
2-[2-pyridylmethylsulfinyl]-(5-hydroxy)benzimidazole,
2-[2-pyridylmethylsulfinyl]-(5-acetyl)benzimidazole, 2-[2-pyridylmethylsulfinyl]-(5-carboxy)benzimidazole,
2-[2-pyridylmethylsulfinyl]-(5-carbethoxy)benzimidazole,
2-[2-(4-chaloro)pyridylmethylsulfinyl]benzimidazole,
2-[2-(5-methyl)pyridylmethylsulfinyl]benzimidazole,
2-[2-pyridylmethylsulfinyl]-N-methylbenzimidazole,
2-[2-pyridyl-(methyl)methylsulfinyl]benzimidazole,
2-[2-pyridylmethylsulfinyl]-(4-methyl)benzimidazole,
2-[2-pyridylmethylsulfinyl]-(N-acetyl)benzimidazole,
2-[2-pyridylmethylsulfinyl]-(N-methoxycarbonyl)benzimidazole,
2-[2-pyridylmethylsulfinyl]-(5-methyl)benximidazole,
2-[2-pyridylmethylsulfinyl]-(5-chloro)benzimidazole,
2-[2-pyridylmethylsulfinyl]-(5-isopropyl)benzimidazole,
2-[2-pyridylmethylsulfinyl]-(5-t-butyl)benzimidazole,
2-[2-pyridylmethylsulfinyl]-(5-n-propyl)benzimidazole,
2-[2-pyridylmethylsulfinyl]-(N-carbamoyl)benzimidazole,
2-[2-pyridylmethylsulfinyl]-(N-methylcarbamoyl)benzimidazole,
2-[2-pyridylmethylsulfinyl]-(N-acetylmethyl)benzimidazole,
2-[2-pyridylmethylsulfinyl]-(N-ethoxycarbonylmethyl)benzimidazole,
2-[2-pyridylmethylsulfinyl]-(N-methylsulfonyl)benzimidazole,
2-[2-(4-methyl)pyridylmethylsulfinyl]-(5-methyl)benzimidazole,
2-[2-(5-methyl)pyridylmethylsulfinyl]-(5-methyl)benzimidazole,
2-[2-pyridylmethylsulfinyl]-(6-chloro)benzimidazole,
2-[2-pyridyl-(ethyl)methylsulfinyl]-benzimidazole,
2-[2-pyridyl-(ethyl)methylsulfinyl]-(5-chloro)benzimidazole,
2-[2-pyridyl-(methyl)methylsulfinyl]-(5-ethyl)benzimidazole,
2-[2-(3-methyl)pyridylmethylsulfinyl]benzimidazole,
2-[2-(5-ethyl)pyridylmethylsulfinyl]-(5-methyl)benzimidazole,
2-[2-(5-ethyl)pyridylmethylsulfinyl]benzimidazole,
2-[2-pyridyl-(ethyl)methylsulfinyl]-(5-ethyl)benzimidazole,
2-[2-pyridyl-(methyl)methylsulfinyl]-(5-methyl)benzimidazole,
2-[2-pyridyl-(methyl)methylsulfinyl]-(5-cyano)benzimidazole,
2-[2-pyridyl-(methyl)methylsulfinyl]-(5-trifluoro)benzimidazole,
2-[2-pyridyl-(ethyl)methylsulfinyl]-(5-methyl)benzimidazole,
2-[2-pyridyl-(ethyl)methylsulfinyl]-(5-cyano)benzimidazole,
2-[2-pyridyl-(ethyl)methylsulfinyl]-(5-trifluoro)benzimidazole,
2-[2-pyridylmethylsulfinyl]-(4-chloro)benzimidazole,
2-[2-pyridyl-(isopropyl)methylsulfinyl]benzimidazole,
2-[2-pyridyl-(methyl)methylsulfinyl]-(5,6-dimethyl)benzimidazole, and
2-[2-pyridyl-methylsulfinyl]-(5,6-dimethyl)benzimidazole.

13. A pharmaceutical composition for inhibiting gastric acid secretion, characterized in that it contains as active agent 0.1 to 95% by weight of a compound of formula I

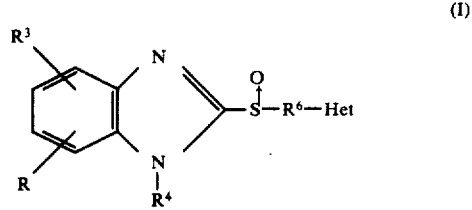

or a therapeutically acceptable non-toxic acid addition salt thereof in a therapeutically effective amount to inhibit gastric acid secretion, in which R selected from the group consisting of hydrogen, alkyl having up to four carbon atoms, halogen of the group consisting of fluoro, iodo, bromo and chloro, cyano, carboxy, carboxyalkyl in which the alkyl group has up to 4 carbon atoms, carboalkoxy in which the alkyl group has up to 4 carbon atoms, carboalkoxyalkyl wherein each of the alkyl groups has up to 4 carbon atoms, carbamoyl, carbamoylalkyl in which the alkyl group has up to 4 carbon atoms, hydroxy, alkoxy having up to 5 carbon atoms, hydroxyalkyl having up to 7 carbon atoms, trifluoromethyl and alkanoyl having up to 4 carbon atoms in any position; $R^3$ is selected from the group consisting of hydrogen, alkyl having up to four carbon atoms, halogen of the group consisting of fluoro, iodo, bromo and chloro, carboxy, carboxyalkyl in which the alkyl group has up to 4 carbon atoms, carboalkoxy in which the alkyl group has up to 4 carbon atoms, carboalkoxyalkyl wherein each of the alkyl groups has up to 4 carbon atoms, carbamoyl, carbamoylalkyl in which the alkyl group has up to 4 carbon atoms, hydroxy, alkoxy having up to 5 carbon atoms, hydroxyalkyl having up to 7 carbon atoms, trifluoromethyl and alkanoyl having up to 4 carbon atoms in any position; $R^4$ is selected from the group consisting of hydrogen alkyl straight or branched chain having up to 5 carbon atoms, alkanoyl having up to 4 carbon atoms, carbamoyl, alkylcarbamoyl wherein the alkyl group may be straight or branched and has up to 4 carbon atoms, dialkylcarbamoyl wherein each alkyl group has up to 4 carbon atoms, alkylcarbonylmethyl wherein the alkyl group has up to 4 carbon atoms, alkoxycarbonylmethyl wherein the alkyl group has up to 4 carbon atoms, and alkylsulphonyl wherein the alkyl group has up to 4 carbon atoms; $R^6$ is a straight branched alkyl group having 1 to 4 carbon atoms, whereby at most one methylene group is present between S and Het, and Het is pyridyl, which may be further substituted preferably in the 3 to 5 position with substituents selected from the group consisting of methyl, ethyl, propyl, chloro and bromo, together with a pharmaceutically acceptable carrier.

14. A pharmaceutical composition according to claim 13, wherein the compound comprises 0.1 to 95% by weight of the preparation.

15. A pharmaceutical composition according to claim 13, in a form suitable for administration by injection wherein the compound comprises about 0.5 to about 20% by weight of the preparation.

16. A pharmaceutical composition according to claim 13 for parenteral application which comprises an aqueous solution of a water soluble salt of said active ingredient in an amount of about 0.5 to 10% by weight of the preparation.

17. A pharmaceutical composition according to claim 13 in a form suitable for oral administration wherein the active ingredient comprises about 2 to about 50% by weight of the preparation.

18. A pharmaceutical composition according to claim 13 in a form suitable for oral administration wherein the dosage of active ingredient is in the range 100 to 400 milligrams per day.

19. A pharmaceutical composition according to claim 13 in a form suitable for intravenous administration wherein the dosage of active ingredient is in the range 5 to 20 milligrams per day.

20. A pharmaceutical composition according to claim 13 wherein the active ingredient is selected from the group consisting of
2-[2-pyridylmethylsulfinyl]benzimidazole,
2-[2-pyridylmethylsulfinyl]-(4,6-dimethyl)benzimidazole,
2-[2-pyridylmethylsulfinyl]-(5-ethyl)benzimidazole,
2-[2-pyridylmethylsulfinyl]-(4-methyl, 6-chloro)benzimidazole,
2-[2-pyridylmethylsulfinyl]-(5-methoxy)benzimidazole,
2-[2-pyridylmethylsulfinyl]-(5-hydroxy)benzimidazole,
2-[2-pyridylmethylsulfinyl]-(5-acetyl)benzimidazole,
2-[2-pyridylmethylsulfinyl]-(5-carboxy)benzimidazole,
2-[2-pyridylmethylsulfinyl]-(5-carbethoxy)benzimidazole,
2-[2-(4-chloro)pyridylmethylsulfinyl]benzimidazole,
2-[2-(5-methyl)pyridylmethylsulfinyl]benzimidazole,
2-[2-pyridylmethylsulfinyl]-N-methylbenzimidazole,
2-[2-pyridyl-(methyl)methylsulfinyl]benzimidazole,
2-[2-pyridylmethylsulfinyl]-(4-methyl)benzimidazole,
2-[2-pyridylmethylsulfinyl]-(N-acetyl)benzimidazole,
2-[2-pyridylmethylsulfinyl]-(N-methoxycarbonyl)benzimidazole,
2-[2-pyridylmethylsulfinyl]-(5-methyl)benzimidazole,
2-[2-pyridylmethylsulfinyl]-(5-chloro)benzimidazole,
2-[2-pyridylmethylsulfinyl]-(5-isopropyl)benzimidazole,
2-[2-pyridylmethylsulfinyl]-(5-t-butyl)benzimidazole,
2-[2-pyridylmethylsulfinyl]-(5-n-propyl)benzimidazole,
2-[2-pyridylmethylsulfinyl]-(N-carbamoyl)benzimidazole,
2-[2-pyridylmethylsulfinyl]-(N-methylcarbamoyl)benzimidazole,
2-[2-pyridylmethylsulfinyl]-(N-acetylmethyl)benzimidazole,
2-[2-pyridylmethylsulfinyl]-(N-ethoxycarbonylmethyl)benzimidazole,
2-[2-pyridylmethylsulfinyl]-(N-methylsulfonyl)benzimidazole,
2-[2-(4-methyl)pyridylmethylsulfinyl]-(5-methyl)benzimidazole,
2-[2-(5-methyl)pyridylmethylsulfinyl]-(5-methyl)benzimidazole,
2-[2-pyridylmethylsulfinyl]-(6-chloro)benzimidazole,
2-[2-pyridyl-(ethyl)methylsulfinyl]benzimidazole,
2-[2-pyridyl-(ethyl)methylsulfinyl]-(5-chloro)benzimidazole,
2-[2-pyridyl-(methyl)methylsulfinyl]-(5-ethyl)benzimidazole,
2-[2-(3-methyl)pyridylmethylsulfinyl]benzimidazole,
2-[2-(5-ethyl)pyridylmethylsulfinyl]-(5-methyl)benzimidazole,
2-[2-(5-ethyl)pyridylmethylsulfinyl]benzimidazole,
2-[2-pyridyl-(ethyl)methylsulfinyl]-(5-ethyl)benzimidazole,
2-[2-pyridyl-(methyl)methylsulfinyl]-(5methyl)benzimidazole,
2-[2-pyridyl-(methyl)methylsulfinyl]-(5-cyano)benzimidazole,
2-[2-pyridyl-(methyl)methylsulfinyl]-(5-trifluoro)benzimidazole,
2-[2-pyridyl-(ethyl)methylsulfinyl]-(5-methyl)benzimidazole,
2-[2-pyridyl-(ethyl)methylsulfinyl]-(5-cyano)benzimidazole,
2-[2-pyridyl-(ethyl)methylsulfinyl]-(5-trifluoro)benzimidazole,
2-[2-pyridylmethylsulfinyl]-(4-chloro)benzimidazole,
2-[2-pyridyl-(isopropyl)methylsulfinyl]benzimidazole,
2-[2-pyridyl-(methyl)methylsulfinyl]-(5,6-dimethyl)benzimidazole, and
2-[2-pyridylmethylsulfinyl]-(5,6-dimethyl)benzimidazole,
and a pharmaceutically acceptable non-toxic addition salt thereof.

21. A pharmaceutical composition according to claim 13 wherein the active ingredient is 2-[2-pyridylmethylsulfinyl]benzimidazole or a pharmaceutically acceptable non-toxic addition salt thereof.

22. A pharmaceutical composition according to claim 13 wherein the active ingredient is 2-[2-pyridylmethylsulfinyl]-(4,6-dimethyl)benzimidazole or a pharmaceutically acceptable non-toxic addition salt thereof.

23. A pharmaceutical composition according to claim 13 wherein the active ingredient is 2-[2-pyridylmethylsulfinyl]-(5-ethyl)benzimidazole or a pharmaceutically acceptable non-toxic, addition salt thereof.

24. A pharmaceutical composition according to claim 13 wherein the active ingredient is 2-[2-pyridylmethylsulfinyl]-(4-methyl,6-chloro)benzimidazole or a pharmaceutically acceptable non-toxic addition salt thereof.

25. A pharmaceutical composition according to claim 13 wherein the active ingredient is 2-[2-pyridylmethylsulfinyl]-(5-methoxy)benzimidazole or a pharmaceutically acceptable non-toxic addition salt thereof.

26. A pharmaceutical composition according to claim 13 wherein the active ingredient is 2-[2-pyridylmethylsulfinyl]-(5-hydroxy)benzimidazole or a pharmaceutically acceptable non-toxic addition salt thereof.

27. A pharmaceutical composition according to claim 13 wherein the active ingredient is 2-[2-pyridylmethylsulfinyl]-(5-acetyl)benzimidazole or a pharmaceutically acceptable non-toxic addition salt thereof.

28. A pharmaceutical composition according to claim 13 wherein the active ingredient is 2-[2-pyridylmethylsulfinyl]-(5-carboxy)benzimidazole or a pharmaceutically acceptable non-toxic addition salt thereof.

29. A pharmaceutical composition according to claim 13 wherein the active ingredient is 2-[2-pyridylmethylsulfinyl]-(5-carbethoxy)benzimidazole or a pharmaceutically acceptable non-toxic addition salt thereof.

30. A pharmaceutical composition according to claim 13 wherein the active ingredient is 2-[2-pyridylmethylsulfinyl]-(N-carbamoyl)benzimidazole or a pharmaceutically acceptable non-toxic addition salt thereof.

31. A pharmaceutical composition according to claim 13 wherein the active ingredient is 2-[2-pyridylmethylsulfinyl]-(N-methylcarbamoyl)benzimidazole or a pharmaceutically acceptable non-toxic addition salt thereof.

32. A pharmaceutical composition according to claim 13 wherein the active ingredient is 2-[2-(4-chloro)-pyridylmethylsulfinyl]benzimidazole or a pharmaceutically acceptable non-toxic addition salt thereof.

33. A pharmaceutical composition according to claim 13 wherein the active ingredient is 2-[2-(5-methyl)-pyridylmethylsulfinyl]benzimidazole or a pharmaceutically acceptable non-toxic addition salt thereof.

34. A pharmaceutical composition according to claim 13 wherein the active ingredient is 2-[2-pyridylmethylsulfinyl]-(N-acetylmethyl)benzimidazole or a pharmaceutically acceptable non-toxic salt thereof.

35. A pharmaceutical composition according to claim 13 wherein the active ingredient is 2-[2-pyridylmethylsulfinyl]-N-methylbenzimidazole or a pharmaceutically acceptable non-toxic addition salt thereof.

36. A pharmaceutical composition according to claim 13 wherein the active ingredient is 2-[2-pyridylmethylsulfinyl]-(N-ethoxycarbonylmethyl)benzimidazole or a pharmaceutically acceptable non-toxic addition salt thereof.

37. A pharmaceutical composition according to claim 13 wherein the active ingredient is 2-[2-pyridylmethylsulfinyl]-(N-methylsulfonyl)benzimidazole or a pharmaceutically acceptable non-toxic addition salt thereof.

38. A pharmaceutical composition according to claim 13 wherein the active ingredient is 2-[2-(4-methyl)-pyridylmethylsulfinyl]-(5-methyl)benzimidazole or a pharmaceutically acceptable non-toxic addition salt thereof.

39. A pharmaceutical composition according to claim 13 wherein the active ingredient is 2-[2-(5-methyl)-pyridylmethylsulfinyl]-(5-methyl)benzimidazole or a pharmaceutically acceptable non-toxic addition salt thereof.

40. A pharmaceutical composition according to claim 13 wherein the active ingredient is 2-[2-pyridylmethylsulfinyl]-(6-chloro)benzimidazole or a pharmaceutically acceptable non-toxic addition salt thereof.

41. A pharmaceutical composition according to claim 13 wherein the active ingredient is 2-[2-pyridyl(ethyl)-methylsulfinyl]benzimidazole or a pharmaceutically acceptable non-toxic addition salt thereof.

42. A pharmaceutical composition according to claim 13 wherein the active ingredient is 2-[2-pyridyl-(methyl)methylsulfinyl]benzimidazole or a pharmaceutically acceptable non-toxic addition salt thereof.

43. A pharmaceutical composition according to claim 13 wherein the active ingredient is 2-[2-pyridylmethylsulfinyl]-(4-methyl)benzimidazole or a pharmaceutically acceptable non-toxic addition salt thereof.

44. A pharmaceutical composition according to claim 13 wherein the active ingredient is 2-[2-pyridyl(ethyl)-methylsulfinyl]-(5-chloro)benzimidazole or a pharmaceutically acceptable non-toxic addition salt thereof.

45. A pharmaceutical composition according to claim 13 wherein the active ingredient is 2-[2-pyridylmethyl)-methylsulfinyl]-(5-ethyl)benzimidazole or a pharmaceutically acceptable non-toxic addition salt thereof.

46. A pharmaceutical composition according to claim 13 wherein the active ingredient is 2-[2-(3-methyl)-pyridylmethylsulfinyl]benzimidazole or a pharmaceutically acceptable non-toxic addition salt thereof.

47. A pharmaceutical composition according to claim 13 wherein the active ingredient is 2-[2-pyridylmethylsulfinyl]-(N-acetyl)benzimidazole or a pharmaceutically acceptable non-toxic addition salt thereof.

48. A pharmaceutical composition according to claim 13 wherein the active ingredient is 2-[2-pyridylmethylsulfinyl]-(N-methoxycarbonyl)benzimidazole or a pharmaceutically acceptable non-toxic addition salt thereof.

49. A pharmaceutical composition according to claim 13 wherein the active ingredient is 2-[2-(5-ethyl)-pyridylmethylsulfinyl]-(5-methyl)benzimidazole or a pharmaceutically acceptable non-toxic addition salt thereof.

50. A pharmaceutical composition according to claim 13 wherein the active ingredient is 2-[2-(5-ethyl)-pyridylmethylsulfinyl]benzimidazole or a pharmaceutically acceptable non-toxic addition salt thereof.

51. A pharmaceutical composition according to claim 13 wherein the active ingredient is 2-[2-pyridyl(ethyl)-methylsulfinyl]-(5-ethyl)benzimidazole or a pharmaceutically acceptable non-toxic addition salt thereof.

52. A pharmaceutical composition according to claim 13 wherein the active ingredient is 2-[2-pyridyl(methyl)methylsulfinyl]-(5-methyl)benzimidazole or a pharmaceutically acceptable non-toxic addition salt thereof.

53. A pharmaceutical composition according to claim 13 wherein the active ingredient is 2-[2-pyridyl(methyl)methylsulfinyl]-(5-cyano)benzimidazole or a pharmaceutically acceptable non-toxic addition salt thereof.

54. A pharmaceutical composition according to claim 13 wherein the active ingredient is 2-[2-pyridyl(methyl)methylsulfinyl]-(5-trifluoromethyl)benzimidazole or a pharmaceutically acceptable non-toxic addition salt thereof.

55. A pharmaceutical composition according to claim 13 wherein the active ingredient is 2-[2-pyridyl(ethyl)-methylsulfinyl]-(5-methyl)benzimidazole or a pharmaceutically acceptable non-toxic addition salt thereof.

56. A pharmaceutical composition according to claim 13 wherein the active ingredient is 2-[2-pyridylmethylsulfinyl]-(5-chloro)benzimidazole or a pharmaceutically acceptable non-toxic addition salt thereof.

57. A pharmaceutical composition according to claim 13 wherein the active ingredient is 2-[2-pyridylmethylsulfinyl]-(5-isopropyl)benzimidazole or a pharmaceutically acceptable non-toxic addition salt thereof.

58. A pharmaceutical composition according to claim 13 wherein the active ingredient is 2-[2-pyridylmethylsulfinyl]-(5-t-butyl)benzimidazole or a pharmaceutically acceptable non-toxic addition salt thereof.

59. A pharmaceutical composition according to claim 13 wherein the active ingredient is 2-[2-pyridylmethylsulfinyl]-(5-n-propyl)benzimidazole or a pharmaceutically acceptable non-toxic addition salt thereof.

60. A pharmaceutical composition according to claim 13 wherein the active ingredient is 2-[2-pyridyl(ethyl)-methylsulfinyl]-(5-cyano)benzimidazole or a pharmaceutically acceptable non-toxic addition salt thereof.

61. A pharmaceutical composition according to claim 13 wherein the active ingredient is 2-[2-pyridyl(ethyl)-methylsulfinyl]-(5-trifluoromethyl)benzimidazole or a pharmaceutically acceptable non-toxic addition salt thereof.

62. A pharmaceutical composition according to claim 13 wherein the active ingredient is 2-[2-pyridylmethylsulfinyl]-(4-chloro)benzimidazole or a pharmaceutically acceptable non-toxic addition salt thereof.

63. A pharmaceutical composition according to claim 13 wherein the active ingredient is 2-[2-pyridyl-(isopropyl)methylsulfinyl]benzimidazole or a pharmaceutically acceptable non-toxic addition salt thereof.

64. A pharmaceutical composition according to claim 13 wherein the active ingredient is 2-[2-pyridyl(methyl)methylsulfinyl]-(5,6-dimethyl)benzimidazole or a pharmaceutically acceptable non-toxic addition salt thereof.

65. A pharmaceutical composition according to claim 13 wherein the active ingredient is 2-[2-pyridylmethylsulfinyl]-(5,6-dimethyl)benzimidazole or a pharmaceutically acceptable non-toxic addition salt thereof.

* * * * *